US006497655B1

(12) United States Patent
Linberg et al.

(10) Patent No.: US 6,497,655 B1
(45) Date of Patent: Dec. 24, 2002

(54) VIRTUAL REMOTE MONITOR, ALERT, DIAGNOSTICS AND PROGRAMMING FOR IMPLANTABLE MEDICAL DEVICE SYSTEMS

(75) Inventors: Kurt R. Linberg, Eden Prairie, MN (US); Randy L. Merry, Maple Groove, MN (US); Chester G. Nelson, Plymouth, MN (US); William J. Plombon, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/466,284

(22) Filed: Dec. 17, 1999

(51) Int. Cl.[7] .................................................. A61B 5/00
(52) U.S. Cl. ...................................... 600/300; 128/904
(58) Field of Search ................................. 600/300, 301; 128/903, 904

(56) References Cited

U.S. PATENT DOCUMENTS

| | | | | |
|---|---|---|---|---|
| 4,146,029 A | * | 3/1979 | Ellinwood, Jr. ........... | 604/891.1 |
| 5,113,869 A | * | 5/1992 | Nappholz et al. ........... | 600/508 |
| 5,995,868 A | * | 11/1999 | Dorfmeister et al. ....... | 600/544 |
| 5,997,476 A | * | 12/1999 | Brown ....................... | 600/300 |
| 6,073,049 A | * | 6/2000 | Alt et al. .................... | 607/31 |
| 6,221,011 B1 | * | 4/2001 | Bardy ........................ | 600/300 |
| 6,250,309 B1 | * | 6/2001 | Krichen et al. ............. | 128/899 |
| 6,363,282 B1 | * | 3/2002 | Nichols ..................... | 607/30 |

* cited by examiner

Primary Examiner—Robert L. Nasser
Assistant Examiner—Patricia C. Mallari
(74) Attorney, Agent, or Firm—Girma Wolde-Michael

(57) ABSTRACT

A plurality of co-operative and complementary software programs are implemented in a web-enabled high speed computer system to remotely monitor, manage and modify the operational and functional parameters of a plurality of implanted medical devices (IMDs). The system utilizes virtual electrophysiologist module (VEM), chronic monitoring module (CMM) and prescription program module (PPM) programs to effect specific therapeutic and diagnostic methods for managing the IMDs, remotely on a conditions and real-time basis. The modules enable remote and continuous monitoring, management and maintenance of the IMDs by identifying critical medical events, determining optimal clinical settings and upgrading performance parameters based on prescriptive data. The modules are implemented in a data center having high-speed computers operating in a web-enabled environment. The modules and the IMDs communicate through wireless communications system via a programmer or an interface medical unit (IMD).

19 Claims, 9 Drawing Sheets

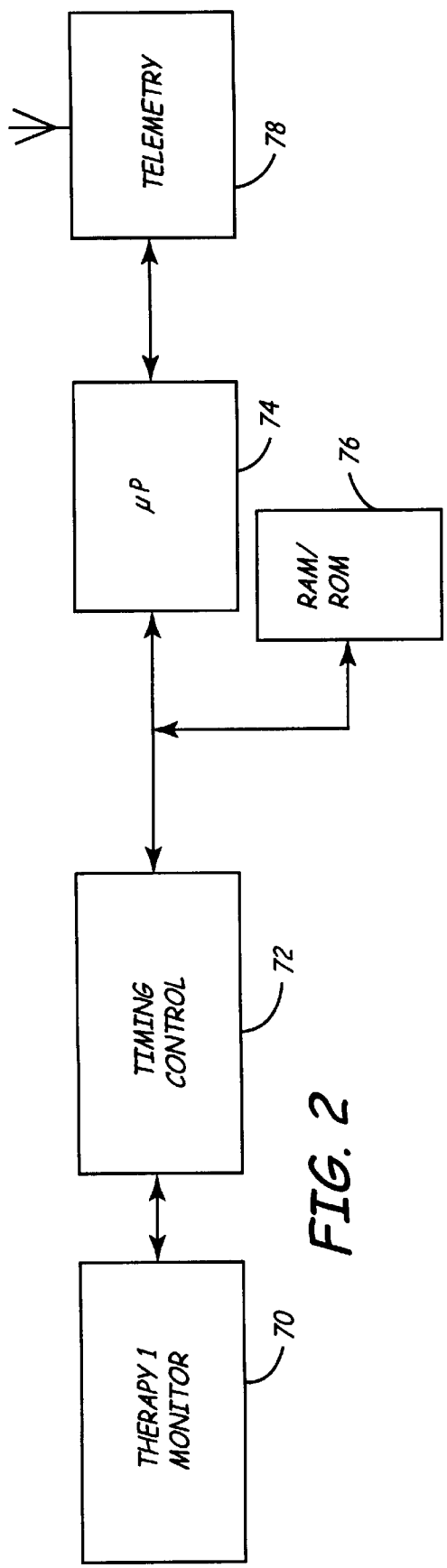
FIG. 2
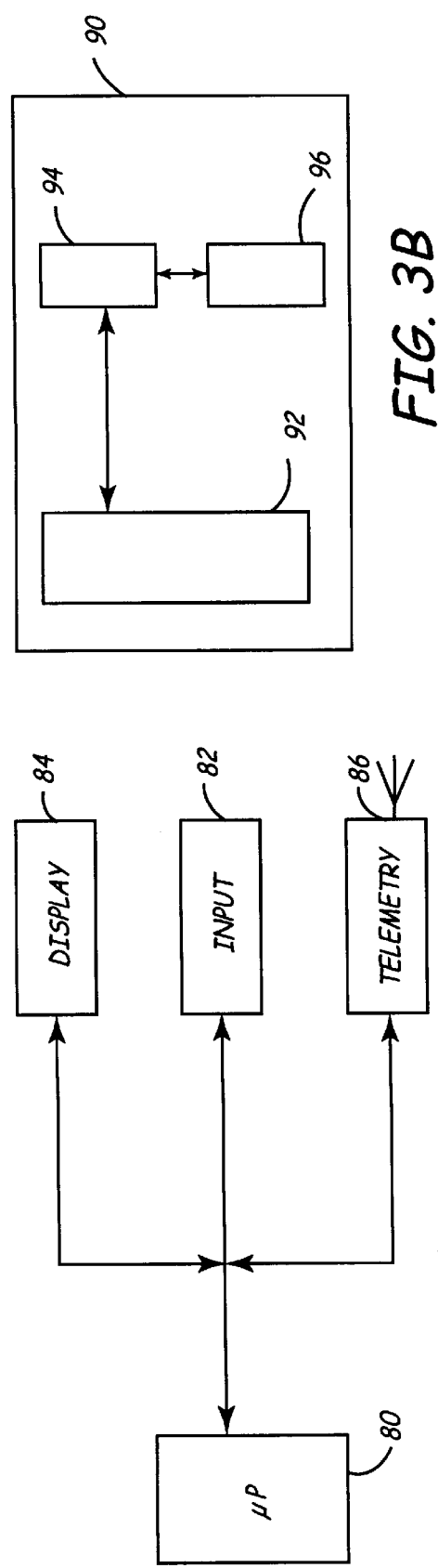
FIG. 3B
FIG. 3A

VIRTUAL REMOTE MONITOR, ALERT, DIAGNOSTICS AND PROGRAMMING FOR IMPLANTABLE MEDICAL DEVICE SYSTEMS

THE FIELD OF THE INVENTION

The present invention relates to medical device systems. Specifically, the invention pertains to a remote bi-directional communications with one or more programmers and medical units, or related controls that are associated with implantable medical devices (IMDs). More specifically, the invention relates to an integrated system and method of bi-directional telecommunications between a web-based expert data center and a medical device, utilizing various types of network platforms and architecture, to implement in the medical device and the IMDs, a virtual electro-physiological monitoring/consultation system, alert activation to initiate a remote monitoring session and prescriptive device programming regimens in real time.

BACKGROUND OF THE INVENTION

A technology-based health care system that fully integrates the technical and social aspects of patient care and therapy should be able to flawlessly connect the client with care providers irrespective of separation distance or location of the participants. While clinicians will continue to treat patients in accordance with accepted modern medical practice, developments in communications technology are making it ever more possible to provide a seamless system of remote patient diagnostics, care and medical services in a time and place independent manner.

Prior art methods of clinical services are generally limited to in-hospital operations. For example, if a physician needs to review the performance parameters of an implantable device in a patient, it is likely that the patient has to go to the clinic. Further, if the medical conditions of a patient with an implantable device warrant a continuous monitoring or adjustment of the device, the patient would have to stay in a hospital indefinitely. Such a continued treatment plan poses both economic and social problems. Under the exemplary scenario, as the segment of the population with implanted medical devices increases many more hospitals/clinics including service personnel will be needed to provide in-hospital service for the patients, thus escalating the cost of healthcare. Additionally the patients will be unduly restricted and inconvenienced by the need to either stay in the hospital or make very frequent visits to a clinic.

Yet another condition of the prior art practice requires that a patient visit a clinic center for occasional retrieval of data from the implanted device to assess the operations of the device and gather patient history for both clinical and research purposes. Such data is acquired by having the patient in a hospital/clinic to down load the stored data from the implantable medical device. Depending on the frequency of data collection this procedure may pose serious difficulty and inconvenience for patients who live in rural areas or have limited mobility. Similarly, in the event a need arises to upgrade the software of an implantable medical device, the patient will be required to come into the clinic or hospital to have the upgrade installed. Further, in medical practice it is an industry-wide standard to keep an accurate record of past and temporaneous procedures relating to an IMD uplink with, for example, a programmer. It is required that the report contain the identification of all the medical devices involved in any interactive procedure. Specifically, all peripheral and major devices that are used in down linking to the IMD need to be reported. Currently, such procedures are manually reported and require an operator or a medical person to diligently enter data during each procedure. One of the limitations of the problems with the reporting procedures is the fact that it is error prone and requires rechecking of the data to verify accuracy.

Yet a further condition of the prior art relates to the operator-programmer interface. Generally a medical device manager/technician, should be trained on the clinical and operational aspects of the programmer. Current practice requires that an operator attend a class/session sponsored by a clinic, hospital or the manufacturer to successfully manage a programmer-IMD procedure. Further, the manager should be able to keep abreast of new developments and new procedures in the management, maintenance and upgrade of the IMD. Accordingly, under current practice it is imperative that operators of programmers, IMDs and related medical devices be trained on a regular basis.

A further limitation of the prior art relates to the management of multiple medical devices in a single patient. Advances in modern patient therapy and treatment have made it possible to implant a number of devices in a patient. For example, IMDs such as a defibrillator or a pacer, a neural implant, a drug pump, a separate physiologic monitor and various other IMDs may be implanted in a single patient. To successfully manage the operations and assess the performance of each device in a patient with multi-implants requires a continuous update and monitoring of the devices. Further, it may be preferred to have an operable communication between the various implants to provide a coordinated clinical therapy to the patient. Thus, there is a need to monitor the IMDs including the programmer on a regular, if not a continuous, basis to ensure optimal patient care. In the absence of other alternatives, this imposes a great burden on the patient if a hospital or clinic is the only center where the necessary upgrade, follow up, evaluation and adjustment of the IMDs could be made. Further, even if feasible, the situation would require the establishment of multiple service areas or clinic centers to support the burgeoning number of multi-implant patients world-wide.

The proliferation of patients with multi-implant medical devices worldwide has made it imperative to provide remote services to the IMDs and timely clinical care to the patient. Frequent use of programmers to communicate with the IMDs and provide various remote services, consistent with co-pending applications titled "System and Method for Transferring Information Relating to an Implantable Medical Device to a Remote Location," filed on Jul. 21, 1999, Ser. No. 09/358,081; "Apparatus and Method for Remote Troubleshooting, Maintenance and Upgrade of Implantable Device Systems," filed on Oct. 26, 1999, Ser. No. 09/426,741; "Tactile Feedback for Indicating Validity of Communication Link with an Implantable Medical Device," filed Oct. 29, 1999, Ser. No. 09/430,708; "Apparatus and Method for Automated Invoicing of Medical Device Systems," filed Oct. 29, 1999, Ser. No. 09/430,208; "Apparatus and Method for Remote Self-Identification of Components in Medical Device Systems," filed Oct. 29, 1999, Ser. No. 09/429,956; "Apparatus and Method to Automate Remote Software Updates of Medical Device Systems," filed Oct. 29, 1999, Ser. No. 09/429,960; "Method and Apparatus to Secure Data Transfer From Medical Device Systems," filed Nov. 2, 1999, Ser. No. 431,881; "Implantable Medical Device Programming Apparatus Having An Auxiliary Component Storage Compartment," filed Nov. 4, 1999, Ser. No. 09/433,477; "Remote Delivery Of Software-Based Training For Implantable Medical Device Systems," filed Nov. 10, 1999, Ser. No. 09/437,615; "Apparatus and Method for Remote Therapy and Diagnosis in Medical Devices Via Interface Systems," filed Dec. 14, 1999, Ser. No. 09/460,580; which are all incorporated by reference herein in their entirety which are all incorporated by reference herein in their entirety, has become an important aspect of patient care. Thus, in light of the referenced disclosures, remote training of the technicians/operators of the programmers and other peripheral equipment, that are associated with the IMDs, is a vital step in providing efficient therapy and clinical care to the patient.

The prior art provides various types of remote sensing and communications with an implanted medical device. One such system is, for example, disclosed in Funke, U.S. Pat. No. 4,987,897 issued Jan. 29, 1991. This patent discloses a system that is at least partially implanted into a living body with a minimum of two implanted devices interconnected by a communication transmission channel. The invention further discloses wireless communications between an external medical device/programmer and the implanted devices.

One of the limitations of the system disclosed in the Funke patent includes the lack of communication between the implanted devices, including the programmer, with a remote clinical station. If, for example, any assessment, monitoring or maintenance is required to be performed on the IMD the patient will have to go to the remote clinic station or the programmer device needs to be brought to the patient's location. More significantly, the operational worthiness and integrity of the programmer cannot be evaluated remotely thus making it unreliable over time as it interacts with the IMD.

Yet another example of sensing and communications system with a plurality of interactive implantable devices is disclosed by Stranberg in U.S. Pat. No. 4,886,064, issued Dec. 12, 1989. In this disclosure, body activity sensors, such as temperature, motion, respiration and /or blood oxygen sensors, are positioned in a patient's body outside a pacer capsule. The sensors wirelessly transmit body activity signals, which are processed by circuitry in the heart pacer. The heart pacing functions are influenced by the processed signals. The signal transmission is a two-way network and allows the sensors to receive control signals for altering the sensor characteristics.

One of the many limitations of Stranberg is the fact that although there is corporeal two-way communications between the implantable medical devices, and the functional response of the heart pacer is processed in the pacer after collecting input from the other sensors, the processor is not remotely programmable. Specifically, the system does not lend itself to web-based communications to enable remote troubleshooting, maintenance and upgrade from outside the patient's body because the processor/programmer is internally located in the patient forming an integral part of the heart pacer.

Yet another prior art reference provides a multi-module medication delivery system as disclosed by Fischell in U.S Pat. No. 4,494,950 issued Jan. 22, 1985. The disclosure relates to a system consisting a multiplicity of separate modules that collectively perform a useful biomedical purpose.

The modules communicate with each other without the use of interconnecting wires. All the modules may be installed intracorporeal or mounted extracorporeal to the patient. In the alternate, some modules may be intracorporeal with others being extracorporeal. Signals are sent from one module to the other by electromagnetic waves. Physiologic sensor measurements sent from a first module cause a second module to perform some function in a closed loop manner. One extracorporeal module can provide electrical power to an intracorporeal module to operate a data transfer unit for transferring data to the external module.

The Fischell disclosure provides modular communication and cooperation between various medication delivery systems. However, the disclosure does not provide an external programmer with remote sensing, remote data management and maintenance of the modules. Further, the system does neither teach nor disclose an external programmer for telemetrically programming the modules.

Yet another example of remote monitoring of implanted cardioverter defibrillators is disclosed by Gessman in U.S. Pat. No. 5,321,618 issued. In this disclosure a remote apparatus is adapted to receive commands from and transmit data to a central monitoring facility over telephone communication channels. The remote apparatus includes equipment for acquiring a patient's ECG waveform and transmitting that waveform to the central facility over the telephone communications channels. The remote apparatus also includes a segment, responsive to a command received from the central monitoring facility, for enabling the emission of audio tone signals from the cardioverter defibrillator. The audio tones are detected and sent to the central monitoring facility via the telephone communication channel. The remote apparatus also includes patient alert devices, which are activated by commands received from the central monitoring facility over the telephone communication channel.

One of the many limitations of the apparatus and method disclosed in the Gessman patent is the fact that the segment, which may be construed to be equivalent to a programmer, is not remotely adjustable from the central monitoring device. The segment merely acts as a switching station between the remote apparatus and the central monitoring station.

An additional example of prior art practice includes a packet-based telemedicine system for communicating information between central monitoring stations and a remote patient monitoring station disclosed in Peifer, WO 99/14882 published Mar. 25, 1999. The disclosure relates to a packet-based telemedicine system for communicating video, voice and medical data between a central monitoring station and a patient that is remotely located with respect to the central monitoring station. The patient monitoring station obtains digital video, voice and medical measurement data from a patient and encapsulates the data in packets and sends the packets over a network to the central monitoring station. Since the information is encapsulated in packets, the information can be sent over multiple types or combination of network architectures, including a community access television (CATV) network, the public switched telephone network (PSTN), the integrated services digital network (ISDN), the Internet, a local area network (LAN), a wide area network (WAN), over a wireless communications network, or over asynchronous transfer mode (ATM) network. A separate transmission code is not required for each different type of transmission media.

One of the advantages of the Pfeifer invention is that it enables data of various forms to be formatted in a single packet irrespective of the origin or medium of transmission. However, the data transfer system lacks the capability to remotely debug the performance parameters of the medical interface device or the programmer. Further, Pfeifer does not disclose a method or structure by which the devices at the patient monitoring station may be remotely updated, maintained and tuned to enhance performance or correct errors and defects.

Another example of a telemetry system for implantable medical devices is disclosed in Duffin et al, U.S. Pat. No. 5,752,976, issued May 19, 1998, incorporated by reference herein in its entirety. Generally, the Duffin et al disclosure relates to a system and method for communicating with a medical device implanted in an ambulatory patient and for locating the patient in order to selectively monitor device function from a remote medical support network. The communications link between the medical support network and the patient communications control device may comprise a world wide satellite network, a cellular telephone network or other personal communications system.

Although the Duffin et al disclosure provides significant advances over the prior art, it does not teach a communications scheme in which a programmer is remotely debugged, maintained, upgraded or modified to ultimately enhance the support it provides to the implantable device with which it is associated. Specifically, the Duffin et al disclosure is limited to notifying remote medical support personnel or an operator about impending problems with an IMD and also enables constant monitoring of the patient's position worldwide using the GPS system. However, Duffin et al does not teach the remote programming scheme contemplated by the present invention.

In a related art, Thompson discloses a patient tracking system in a co-pending application entitled "World-wide Patient Location and Data Telemetry System For Implantable Medical Devices", Ser. No. 09/045,272, filed on Mar. 20, 1998 which is incorporated by reference herein in its entirety. The disclosure provides additional features for patient tracking in a mobile environment worldwide via the GPS system. However, the remote programming concepts advanced by the present invention are not within the purview of the Thompson disclosure because there is no teaching of a web-based environment in which an implantable medical device is remotely evaluated and monitored to effect functional and parametric tune up, upgrade and maintenance as needed.

Yet in another related art, Ferek-Petric discloses a system for communication with a medical device in a co-pending application, Ser. No. 09/348,506 which is incorporated by reference herein in its entirety. The disclosure relates to a system that enables remote communications with a medical device, such as a programmer. Particularly, the system enables remote communications to inform device experts about programmer status and problems, The experts will then provide guidance and support to the remotely to service personnel or operators located at the programmer. The system may include a medical device adapted to be implanted into a patient; a server PC communicating with the medical device; the server PC having means for receiving data transmitted across a dispersed data communication pathway, such as the Internet; and a client PC having means for receiving data transmitted across a dispersed communications pathway from the SPC. In certain configurations the server PC may have means for transmitting data across a dispersed data communication pathway (Internet) along a first channel and a second channel; and the client PC may have means for receiving data across a dispersed communication pathway from the server PC along a first channel and a second channel.

One of the significant teachings of Ferek-Petric's disclosure, in the context of the present invention, includes the implementation of communication systems, associated with IMDs that are compatible with the Internet. Specifically the disclosure advances the art of remote communications between a medical device, such as a programmer, and experts located at a remote location using the Internet. As indicated hereinabove, the communications scheme is structured to primarily alert remote experts to existing or impending problems with the programming device so that prudent action, such as early maintenance or other remedial steps, may be timely exercised. Further, because of the early warning or advance knowledge of the problem, the remote expert would be well informed to provide remote advice or guidance to service personnel or operators at the programmer.

While Ferek's invention advances the art in communications systems relating to interacting with a programmer via a communication medium such as the Internet, the system does neither propose nor suggest remote programming, debugging and maintenance of a programmer without the intervention of a service person.

Another disclosure relating to ambulatory patient health monitoring techniques utilizing interactive visual communications is disclosed by Daniel et al in U.S. Pat. No. 5,441,047, issued Aug. 15, 1995. The invention relates to a system in which the patient is monitored by a health care worker at a certain station, while the patient is at a remote location. The patient's condition is monitored in the home using various monitoring devices. The health care worker is placed into interactive visual communication with the patient.

Yet another prior art provides a monitoring method and a monitoring equipment in U.S. Pat. No. 5,840,020 by Pekka et al issued on Nov. 24, 1998. The patent relates to a monitoring equipment including means for receiving a measurement result indicating the patients blood glucose level, and for storing it in memory. In order to improve and facilitate the treatment of the patient, the monitoring equipment further includes means for receiving data concerning the patient's diet, medication and physical strain and for storing it in the memory. A series of calculations are refined to provide predictive values Further, another prior art provides a method for monitoring the health of a patient as disclosed in U.S. Pat. No. 5,772,586 issued to Pekka et al on Jun. 30, 1998. The disclosure relates to a method for monitoring the health of a patient by utilizing measurements. In order to improve the contact between the patient and the person treating him, the results of the measurements are supplied via a communications device utilizing a wireless data transmission link to a data processing system available to the person monitoring the patient's health. The patient's health is monitored by means of the data stored in the data processing system.

Yet a further example of a prior art is provided in U.S. Pat. No. 5,701,904 by Simmons et al issued on Dec. 30, 1997 relating to telemedicine instrumentation pack. The invention includes a portable medical diagnostic apparatus for data gathering. A video camera generates signals based on images taken from the visual instruments. Other electronics circuitry generates signals based on output of the audio instrument and data-gathering instruments. The signals are transmitted to a remote site for analysis by medical personnel.

A related prior art is disclosed in U.S. Pat. No. 5,434,611 issued to Tamura on Jul. 18, 1995. The disclosure relates to a health care system which employs a two-way communications antenna television network to permit communication between a doctor and patients at different locations. The system utilizes a community antenna television (CATV) so that the doctor can directly interrogate patients at home, and the patients can be automatically monitored at home using images and voice by the doctor in the medical office, without hindrance to normal CATV broadcasting.

Yet another related prior art is disclosed in U.S. Pat. No. 5,791,907 by Ramshaw issued on Aug. 11, 1998. The disclosure relates to an interactive medical training device including a computer system with a display. The computer is programmed to provide education and training in medical procedures.

Another related prior art is disclosed in U.S. Pat. No. 5,810,747 by Brudny et al. issued on Sep. 22, 1998. The invention relates to an interactive intervention training system used for monitoring a patient. An expert system and a neural network determine a goal to be achieved during training.

One of the limitations of Brudny's teachings is the fact that the interactive training does not provide for a programmer type interface between the expert system (remote station) and a plurality of IMDs. Further, there is no software structure or scheme to provide the various remote programming functions contemplated by the present invention.

Some of the limitations of Ramshaw's disclosure, in light of the present invention, include the fact that there is no teaching of a program that is used for managing implantable devices to effect various clinical procedures and therapy based on a remotely transmitted interactive software from a web-based data center.

Further U.S. Pat. No. 5,590,057 by Ruuska et al., issued on Dec. 31, 1996 provides a training and certification system for a user to perform a task. The invention includes an input device, output device and a controller. The controller receives input data from the input device and controls the output displayed on the output device. The system presents a user with a pretest, a module containing instructions, information about a certain portion of the task to be performed, as well as mini-simulations and a variety of questions. The system present a post-test result and determines if the user is certifiable.

Ruuska et al's disclosure relates to training on a task and provides an advance in computer implemented system for training and certifying a trainee to perform a task. However, in light of the present invention, Ruuska et al. has several limitations. Specifically, Ruuska does not disclose a programmer for managing the operations of IMDs. Further, Ruuska does not relate to a highly globally distributed number of programmers on which technicians need to be trained to operate both the programmers and the IMDs. In the present invention, each programmer may manage a plurality of IMDs via, preferably, a telemetric data transmission system. IMD data download, new software installation, patient history, including significant clinical/ therapy information are routinely exchanged between the programmer and the IMDs using the program modules implemented by the present invention. The globally distributed programmers that manage the IMDs locally are connected, via a bi-directional communications link, to a remote data center to exchange data, voice and video. The remote data center is a universal command/control point in which expert system's reside.

Accordingly, it would be advantageous to provide a system in which a programmer could uplink to a remote expert data center to import enabling software for self-diagnosis, maintenance and upgrade of the programmer. Yet another desirable advantage would be to provide a system to implement the use of remote expert systems to manage a programmer on a real-time basis. A further desirable advantage would be to provide a communications scheme that is compatible with various communications media, to promote a fast uplink of a programmer to remote expert systems and specialized data resources. Yet another desirable advantage would be to provide a high speed communications scheme to enable the transmission of high fidelity sound, video and data to advance and implement efficient remote data management of a clinical/therapy system via a programmer or an interface medical device thereby enhancing patient clinical care. Preferably, a remote web-based expert data center would direct, command and control the clinical, therapeutic and operational functions of a multiple set of implantable medical devices, on a continuous and real time basis, utilizing a high speed communication scheme. As discussed herein below, the present invention provides these and other desirable advantages.

SUMMARY OF THE INVENTION

The present invention generally relates to a communications scheme in which a remote web-based expert data center interacts with a patient having one or more implantable medical devices (IMDs) via an associated external medical device, preferably a programmer, located in close proximity to the IMDs. Some of the most significant advantages of the invention include the use of various communications media between the remote web-based expert data center, the programmer and an interface medical unit to remotely exchange clinically significant information and ultimately effect real-time parametric and operational changes in the IMDs as needed.

In the context of the present invention, one of the many aspects of the invention includes a real-time access of a programmer to a remote web-based expert data center, via a communication network, which includes the Internet. The operative structure of the invention includes the remote web-based expert data center, in which an expert system is maintained, having a bi-directional real-time data, sound and video communications with the programmer via a broad range of communication link systems. The programmer is in turn in telemetric communications with the IMDs such that the IMDs may uplink to the programmer or the programmer may down link to the IMDs, as needed.

In yet another context of the invention, the critical components and embedded systems of the programmer are remotely maintained, debugged and/or evaluated to ensure proper functionality and performance by down linking expert systems and compatible software from the web-based expert data center.

In a further context of the invention, a programmer or an interface medical unit is remotely monitored, assessed and upgraded as needed by importing software from a remote expert data center via a wireless or equivalent communications system. The operational and functional software of the embedded systems in the programmer or the interface medical unit may be remotely adjusted, upgraded or changed as apparent. The software changes installed in the programmer/ interface medical unit may ultimately be implemented in the IMDs as needed by down linking to the IMDs.

Yet another context of the invention includes a communications scheme that provides a highly integrated and efficient method and structure of clinical information management in which various networks such as Community access Television, Local area Network (LAN), a wide area network (WAN) Integrated Services Digital Network (ISDN), the Public Switched telephone Network (PSTN), the Internet, a wireless network, an asynchronous transfer mode (ATM) network, a laser wave network, satellite, mobile and other similar networks are implemented to transfer voice, data and video between the remote data center and a programmer. In the preferred embodiment, wireless communications systems, a modem and laser wave systems are illustrated as examples only and should be viewed without limiting the invention to these types of communications alone. Further, in the interest of simplicity, the applicants refer to the various communications system, in relevant parts, as a communications system. However, it should be noted that the communication systems, in the context of this invention, are interchangeable and may relate to various schemes of cable, fiber optics, microwave, radio, laser and similar communications or any practical combinations thereof.

Some of the distinguishing features of the present invention include the use of a robust web-based expert data center to manage and tune the operational and functional parameters of a plurality of IMDs in real-time. Specifically, the invention enables remote diagnosis, maintenance, upgrade, performance tracking, tuning and adjustment of the IMDs via a programmer. One additional benefit of the present invention is an enhancement of the IMDs using a prescriptive program data set to be implemented, on a proactive basis, in the IMDs by down linking from the programmer thereby upgrading the IMDs to promote the patient's well being.

Yet one of the other distinguishing features of the invention includes the use a highly flexible and adaptable communications scheme to promote continuous and real-time communications between a remote expert data center and a programmer associated with a plurality of IMDs. The IMDs are structured to share information intracorporeally and may interact with the programmer, as a unit. Specifically, the IMDs either jointly or severally can be interrogated to implement or extract clinical information as required. In other words, all of the IMDs may be accessed via one IMD or, in the alternate, each one of the IMDs may be accessed individually. The information collected in this manner may be transferred to the programmer by up linking the IMDs as needed.

Further, the present invention provides significant advantages over the prior art by enabling remote troubleshooting, maintenance and software upgrade to the IMDs. The communications scheme enables remote debugging and analysis of the IMDs via the programmer. In the event a component or software defect is noted, the system is able to check whether a 'remote-fix' is possible. If not, the system broadcasts an alert to an operator thus attending to the problem on a real-time basis. In the execution of this function the communications scheme of the present invention performs, inter alia, a review of usage logs, error logs, power and battery status, data base integrity and the mean time between failures status of all the significant and relevant components. Further, patient history, performance parameter integrity and software status are mined from the IMDs via programmer's database and analyzed by an analyzer at the remote expert data center.

The invention provides significant compatibility and scalability to other web-based applications such as telemedicine and emerging web-based technologies such as tele-immersion. For example, the system may be adapted to interface with medical applications in which an interface medical unit may be used to uplink the patient to a remote data center for information exchange between the IMDs and the remote expert data center. More significantly, the invention provides a system and method to remotely install various operational and functional software in the IMDs via a surrogate device which is tailored to provide the required functional capabilities to manage the IMDs.

Specifically, the invention implements a virtual electrophysiologist module (VEM), a chronic monitor module (CMM) and prescriptive program module (PPM) to remotely program IMDs via a programmer or an interface medical unit. The remote communication is facilitated by a web-enabled system utilizing various types of high speed communication media to effect real-time clinical care and therapy to patients with IMDs.

BRIEF DESCRIPTION OF THE DRAWINGS

The present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIG. 2 is a block diagram representing the major components of an IMD;

FIG. 3A is a block diagram representing the major components of a programmer or interface medical device;

FIG. 3B is a block diagram representing a laser transceiver for high speed transmission of voice, video and other data;

DESCRIPTION OF THE PREFERRED EMBODIMENTS

Figure 1:
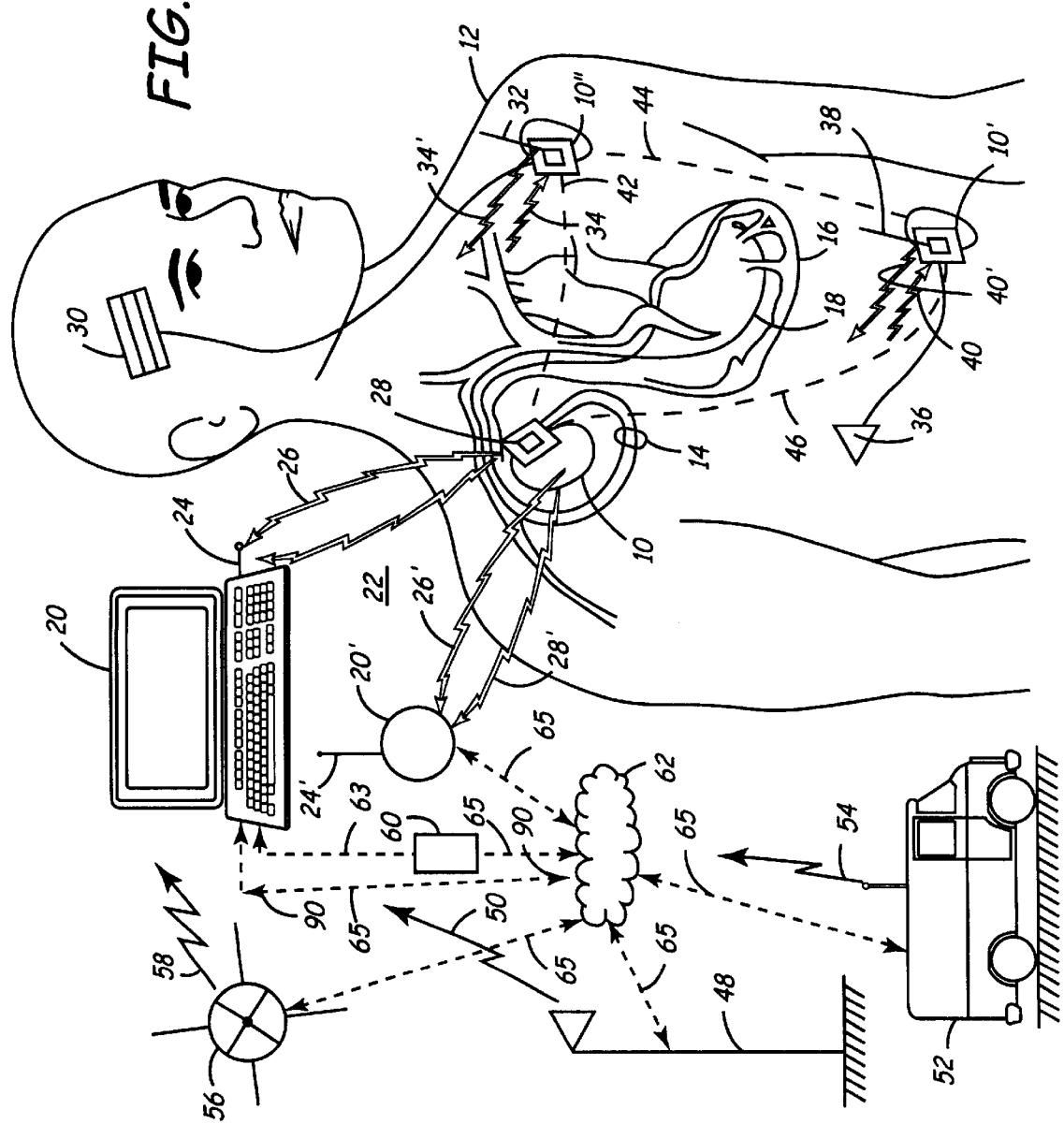
FIG. 1 is a simplified schematic diagram of major uplink and downlink telemetry communications between a remote clinical station, a programmer and a plurality of implantable medical devices (IMDs)

FIG. 1 is a simplified schematic of the major components of the present invention. Specifically, a bi-directional wireless communications system between programmer 20, interface medical unit 20' and a number of implantable medical devices (IMDS) represented by IMD 10, IMD 10' and IMD 10" is shown. The IMDs are implanted in patient 12 beneath the skin or muscle. The IMDs are electrically coupled to electrodes 18, 3 0, and 3 6 respectively in a manner known in the art. IMD 10 contains a microprocessor for timing, sensing and pacing functions consistent with preset programmed functions. Similarly, IMDs 10' and 10" are microprocessor-based to provide timing and sensing functions to execute the clinical functions for which they are employed. For example, IMD 10' could provide neural stimulation to the brain via electrode 30 and IMD 10" may function as a drug delivery system that is controlled by electrode 36. The various functions of the IMDs are coordinated using wireless telemetry. Wireless links 42, 44 and 46 jointly and severally couple IMDs 10, 10' and 10" such that programmer 20 may transmit commands or data to any or all the of IMDs via one of telemetry antennas 28, 32 and 38. This structure provides a highly flexible and economical wireless communications system between the IMDS. Further, the structure provides a redundant communications system, which enables access to any one of a multiplicity of IMDs in the event of a malfunction of one or two of antennas 28, 32 and 38.

Programming commands or data are transmitted from programmer 20 to IMDs 10, 10' and 10" via external RF telemetry antenna 24. Telemetry antenna 24 may be an RF head or equivalent. Antenna 24 may be located on programmer 20 externally on the case or housing. Telemetry antenna 24 is generally telescoping and may be adjustable on the case of programmer 20. Both programmer 20 and interface medical unit 20' may be placed a few feet away from patient 12 and would still be within range to wirelessly communicate with telemetry antennas 28, 32 and 38.

The uplink to remote web-based expert data center 62, hereinafter referred to as, interchangeably, "data center 62", "expert data center 62" or "web-based data center 62" without limitations, is accomplished through programmer 20 or interface medical unit 20'. Accordingly programmer 20 and interface medical unit 20' function as an interface between IMDs 10, 10' and 10" and data center 62. One of the many distinguishing elements of the present invention includes the use of various scalable, reliable and high-speed wireless communication systems to bi-directionally transmit high fidelity digital/analog data between programmer 20 and data center 62.

There are a variety of wireless mediums through which data communications could be established between programmer 20 or interface medical unit 20' and data center 62. The communications link between Programmer 20 or interface medical unit 20' and data center 62 could be modem 60, which is connected to programmer 20 on one side at line 63 and data center 62 at line 64 on the other side. In this case, data is transferred from data center 62 to programmer 20 via modem 60. Alternate data transmission systems include, without limitations, stationary microwave and/or RF antennas 48 being wirelessly connected to programmer 20 via tunable frequency wave delineated by line 50. Antenna 48 is in communications with data center 62 via wireless link 65. Similarly, interface medical unit 20', mobile vehicle 52 and satellite 56 are in communications with data center 62 via wireless link 65. Further, mobile system 52 and satellite 56 are in wireless communications with programmer 20 or interface medical unit 20' via tunable frequency waves 54 and 58, respectively.

In the preferred embodiment a Telnet system is used to wirelessly access data center 62. Telnet emulates a client/server model and requires that the client run a dedicated software to access data center 62. The Telnet scheme envisioned for use with the present invention includes various operating systems including UNIX, Macintosh, and all versions of Windows.

Functionally, an operator at programmer 20 or an operator at data center 62 would initiate remote contact. Programmer 20 is down linkable to IMDs via link antennas 28, 32 and 38 to enable data reception and transmission. For example, an operator or a clinician at data center 62 may downlink to programmer 20 to perform a routine or a scheduled evaluation of programmer 20. In this case the wireless communication is made via wireless link 65. If a downlink is required from programmer 20 to IMD 10 for example, the downlink is effected using telemetry antenna 22. In the alternate, if an uplink is initiated from patient 12 to programmer 20 the uplink is executed via wireless link 26. As discussed herein below, each antenna from the IMDs can be used to uplink all or one of the IMDs to programmer 20. For example, IMD 10' which relates to neural implant 30 can be implemented to up-link, via wireless antenna 34 or wireless antenna 34', any one, two or more IMDs to programmer 20. Preferably bluetooth chips, adopted to function within the body to outside the body and also adopted to provide low current drain, are embedded in order to provide wireless and seamless connections 42, 44 and 46 between IMDs 10, 10' and 10". The communication scheme is designed to be broadband compatible and capable of simultaneously supporting multiple information sets and architecture, transmitting at relatively high speed, to provide data, sound and video services on demand.

FIG. 2 illustrates typical components of an IMD, such as those contemplated by the present invention. Specifically, major operative structures common to all IMDs 10, 10' and 10" are represented in a generic format. In the interest of brevity, IMD 10 relative to FIG. 2 refers to all the other IMDs. Accordingly, IMD 10 is implanted in patient 12 beneath the patient's skin or muscle and is electrically coupled to heart 16 of patient 12 through pace/sense electrodes and lead conductor(s) of at least one cardiac pacing lead 18 in a manner known in the art. IMD 10 contains timing control 72 including operating system that may employ microprocessor 74 or a digital state machine for timing, sensing and pacing functions in accordance with a programmed operating mode. IMD 10 also contains sense amplifiers for detecting cardiac signals, patient activity sensors or other physiologic sensors for sensing the need for cardiac output, and pulse generating output circuits for delivering pacing pulses to at least one heart chamber of heart 16 under control of the operating system in a manner well known in the prior art. The operating system includes memory registers or RAM/ROM 76 for storing a variety of programmed-in operating mode and parameter values that are used by the operating system. The memory registers or RAM/ROM 76 may also be used for storing data compiled from sensed cardiac activity and/or relating to device operating history or sensed physiologic parameters for telemetry out on receipt of a retrieval or interrogation instruction. All of these functions and operations are well known in the art, and many are generally employed to store operating commands and data for controlling device operation and for later retrieval to diagnose device function or patient condition.

Programming commands or data are transmitted between IMD 10 RF telemetry antenna 28, for example, and an external RF telemetry antenna 24 associated with programmer 20. In this case, it is not necessary that the external RF telemetry antenna 24 be contained in a programmer RF head so that it can be located close to the patient's skin overlying IMD10. Instead, the external RF telemetry antenna 24 can be located on the case of programmer 20. It should be noted that programmer 20 can be located some distance away from patient 12 and is locally placed proximate to the IMDs such that the communication between IMDs 10, 10' and 10" and programmer 20 is telemetric. For example, programmer 20 and external RF telemetry antenna 24 may be on a stand a few meters or so away from patient 12. Moreover, patient 12 may be active and could be exercising on a treadmill or the like during an uplink telemetry interrogation of real-time ECG or other physiologic parameters. Programmer 20 may also be designed to universally program existing IMDs that employ RF telemetry antennas of the prior art and therefore also have a conventional programmer RF head and associated software for selective use therewith.

In an uplink communication between IMD 10 and programmer 20, for example, telemetry transmission 22 is activated to operate as a transmitter and external RF telemetry antenna 24 operates as a telemetry receiver. In this manner data and information may be transmitted from IMD10 to programmer 20. In the alternate, IMD 10 RF telemetry antenna 26 operates as a telemetry receiver antenna to downlink data and information from programmer 20. Both RF telemetry antennas 22 and 26 are coupled to a transceiver comprising a transmitter and a receiver.

FIG. 3A is a simplified circuit block diagram of major functional components of programmer 20. The external RF telemetry antenna 24 on programmer 20 is coupled to a telemetry transceiver 86 and antenna driver circuit board including a telemetry transmitter and telemetry receiver 34. The telemetry transmitter and telemetry receiver are coupled to control circuitry and registers operated under the control of microcomputer 80. Similarly, within IMD 10, for example, the RF telemetry antenna 26 is coupled to a telemetry transceiver comprising a telemetry transmitter and telemetry receiver. The telemetry transmitter and telemetry receiver in IMD 10 are coupled to control circuitry and registers operated under the control of microcomputer 74.

Further referring to FIG. 3A, programmer 20 is a personal computer type, microprocessor-based device incorporating a central processing unit, which may be, for example, an Intel Pentium microprocessor or the like. A system bus interconnects CPU 80 with a hard disk drive, storing operational programs and data, and with a graphics circuit and an interface controller module. A floppy disk drive or a CD ROM drive is also coupled to the bus and is accessible via a disk insertion slot within the housing of programmer 20. Programmer 20 further comprises an interface module, which includes a digital circuit, a non-isolated analog circuit, and an isolated analog circuit. The digital circuit enables the interface module to communicate with interface controller module. Operation of the programmer in accordance with the present invention is controlled by microprocessor 80.

In order for the physician or other caregiver or operator to communicate with the programmer 20, a keyboard or input 82 coupled to CPU 80 is optionally provided. However the primary communications mode may be through graphics display screen of the well-known "touch sensitive" type controlled by a graphics circuit. A user of programmer 20 may interact therewith through the use of a stylus, also coupled to a graphics circuit, which is used to point to various locations on screen or display 84 which display menu choices for selection by the user or an alphanumeric keyboard for entering text or numbers and other symbols. Various touch-screen assemblies are known and commercially available. Display 84 and or the keyboard comprise means for entering command signals from the operator to initiate transmissions of downlink or uplink telemetry and to initiate and control telemetry sessions once a telemetry link with data center 62 or an implanted device has been established. Display screen 84 is also used to display patient related data and menu choices and data entry fields used in entering the data in accordance with the present invention as described below. Display screen 84 also displays a variety of screens of telemetered out data or real-time data. Display screen 84 may also display plinked event signals as they are received and thereby serve as a means for enabling the operator to timely review link-history and status.

Programmer 20 further comprises an interface module, which includes digital circuit, non-isolated analog circuit, and isolated analog circuit. The digital circuit enables the interface module to communicate with the interface controller module. As indicated hereinabove, the operation of programmer 20, in accordance with the present invention, is controlled by microprocessor 80. Programmer 20 is preferably of the type that is disclosed in U.S Pat. No. 5,345,362 to Winkler, which is incorporated by reference herein in its entirety.

Screen 84 may also display up-linked event signals when received and thereby serve as a means for enabling the operator of programmer 20 to correlate the receipt of uplink telemetry from an implanted device with the application of a response-provoking action to the patient's body as needed. Programmer 20 is also provided with a strip chart printer or the like coupled to interface controller module so that a hard copy of a patient's ECG, EGM, marker channel of graphics displayed on the display screen can be generated.

As will be appreciated by those of ordinary skill in the art, it is often desirable to provide a means for programmer 20 to adapt its mode of operation depending upon the type or generation of implanted medical device to be programmed and to be compliant with the wireless communications system through which data and information is transmitted between programmer 20 and data center 62.

FIG. 3B is an illustration of the major components of Wave unit 90 utilizing laser technologies such as for example the WAVESTAR Optic Air Unit, manufactured by Lucent Technologies or equivalent. This embodiment may be implemented for large data transfer at high speed in applications involving several programmers. The unit includes laser 92, transceiver 94 and amplifier 96. A first wave unit 90 is installed at data center 62 and a second unit 90' is located proximate to programmer 20 or interface medical unit (IMU) 20'. Data transmission between remote data center 62 and programmer unit 20 is executed via wave units 90. Typically, the first wave unit 90 accepts data and splits it into unique wavelength for transmission. The second wave unit 90' recomposes the data back to its original form.

Figure 4:
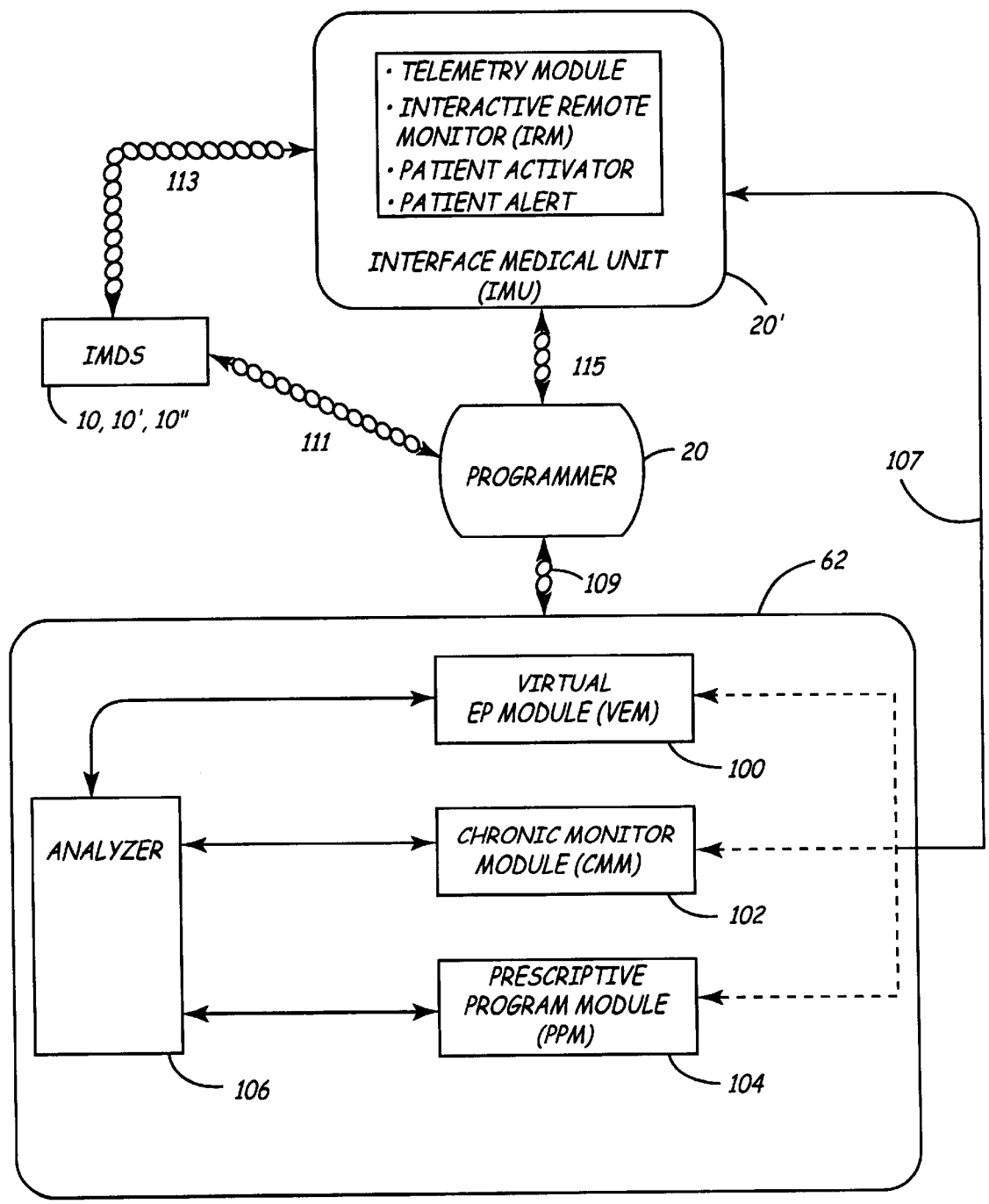
FIG. 4 is a block diagram illustrating the organizational structure of the wireless communication system in accordance with the present invention.

FIG. 4 is a simplified block diagram illustrating the principal systems of the present invention. In the context of the present invention, the data center also includes virtual electrophysiologist module (VEM) 100, chronic monitoring module (CMM) 102, and prescriptive program module (PPM) 104 each being in a two-way communication with analyzer 106. As discussed hereinabove, data center 62 is preferably in wireless communications with programmer 20. The medium of communications between programmer 20 and data center 62 may be selected from one or a combination of several cable and wireless systems discussed hereinabove. Further, programmer 20 is in wireless communications with a number of IMDs, such as shown in FIG. 1. Although three IMDs are shown for illustrative purposes, it should be noted that several IMDs may be implemented and the practice of the present invention does not limit the number of implants per se. Data center 62 is in wireless communications with programmer 20 via link 109. Further, programmer 20 is in wireless data communications with IMDs 10, 10' and 10" and IMU 20' via links 11 and 115 respectively. As will discussed herein below, in an alternate embodiment relating to special applications, IMU 20' could be in direct wireless or data communications with data center 62 and IMDs 10, 10' and 10" via links 107 and 113 respectively.

Figure 5:
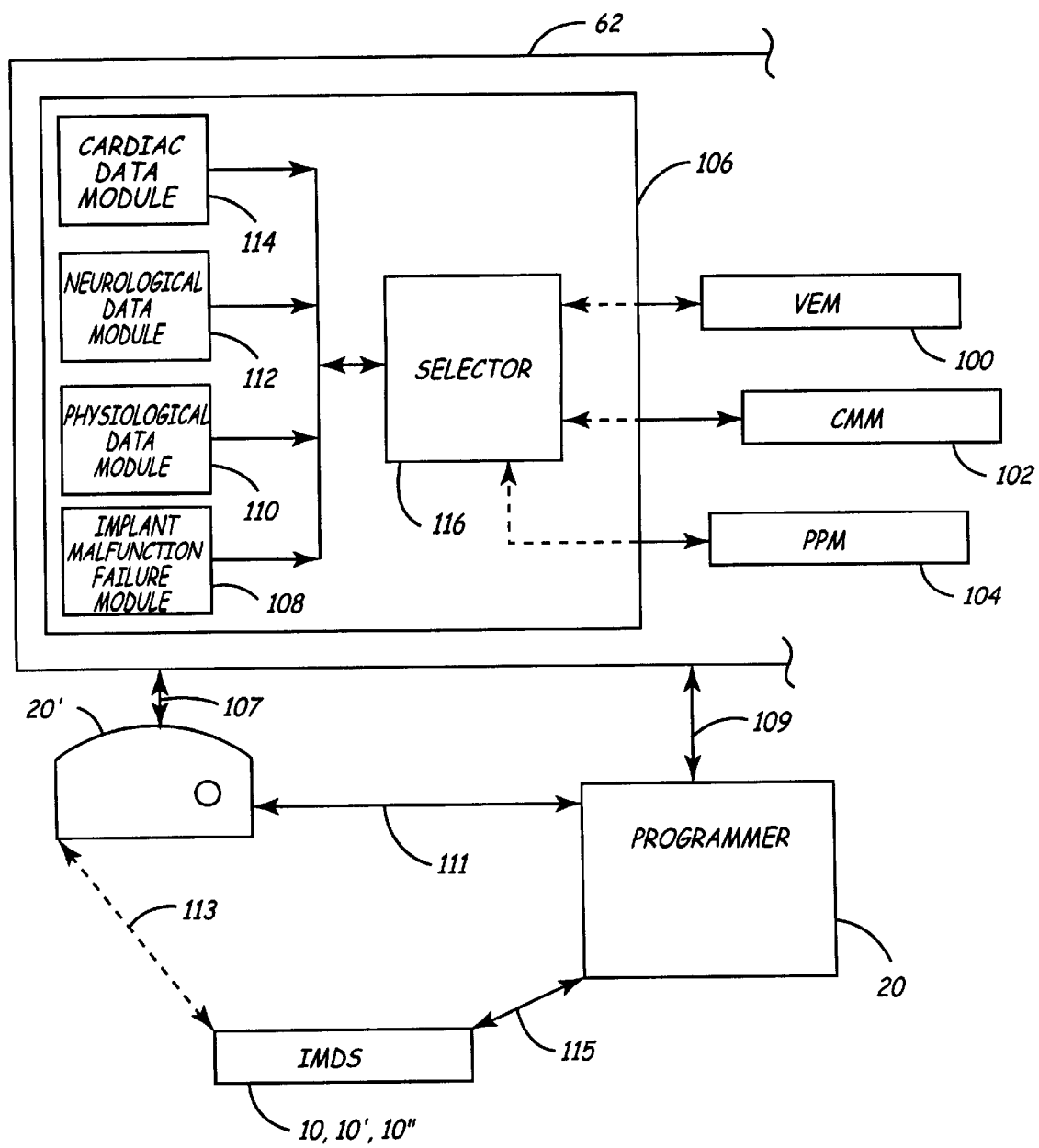
FIG. 5 is a block diagram illustrating a detail section of specific components used in the present invention.

FIG. 5 is a detail representation of the relevant elements of analyzer 106. Specifically, in the context of the present invention, analyzer 106 includes implant device malfunction or failure alert module 108, physiological data module 110, neurological data module 112 and cardiac data module 114. It should be noted that several other modules could be added to expand the modular elements of analyzer 106 depending upon the need for as many modules. The modules are in a bi-directional data and electronic connection with selector 116. Further, selector 116 is in operable two-way data communication with VEM 100, CMM 102 and PPM 104. As indicated hereinabove, programmer 20 is in a bi-directional wireless communications with data center 62 via link 109. Programmer 20 is also in a two-way wireless communication with IMDs 10, 10' and 10" and IMU20' via links 115 and 111 respectively.

Referring to programmer 20 in more detail, when a physician or an operator needs to interact with programmer 20, a keyboard coupled to Processor 80 is optionally employed. However the primary communication mode may be through graphics display screen of the well-known "touch sensitive" type controlled by graphics circuit. A user of programmer 20 may interact therewith through the use of a stylus also coupled to a graphics circuit, which is used to point to various locations on screen/display to display menu choices for selection by the user or an alphanumeric keyboard for entering text or numbers and other symbols as shown in the above-incorporated '362 patent. Various touch-screen assemblies are known and commercially available. The display and or the keyboard of programmer 20, preferably include means for entering command signals from the operator to initiate transmissions of downlink telemetry from IMDs and to initiate and control telemetry sessions once a telemetry link with one or more IMDs has been established. A graphics display /screen is also used to display patient related data and menu choices and data entry fields used in entering the data in accordance with the present invention as described below. The graphics display/screen also displays a variety of screens of telemetered out data or real-time data. Programmer 20 is also provided with a strip chart printer or the like coupled to interface controller module so that a hard copy of a patient's ECG, EGM, marker channel or similar graphics display can be generated. Further, the functional and data communications event and history of programmer 20 relating to instrumentation and software status may be printed from a printer. Similarly, once an uplink is established between programmer 20 and any one of IMDs 10, 10' and 10", various patient history data and IMD performance data may be printed out. The IMDs contemplated by the present invention include a cardiac pacemaker, a defibrillator, a pacer-defibrillator, implantable monitor, cardiac assist device, and similar implantable devices for cardiac rhythm and therapy. Further the IMD units contemplated by the present invention include electrical stimulators such as, but not limited to, a drug delivery system, a neural stimulator, a neural implant, a nerve or muscle stimulator or any other implant designed to provide physiologic assistance or clinical therapy.

As indicated hereinabove, data center 62 represents a high speed computer network system which is located remotely via wireless bi-directional data, voice and video communications with programmer 20 and, in special cases with IMU 20'. Generally data center 62 is preferably located in a central location and is equipped with high-speed web-based, web-enabled or web-compatible computer networks. Preferably, data center 62 is manned 24-hours by operators and clinical personnel who are trained to provide a web-based remote service to programmer 20 and IMU 20' to thereby ensure chronic monitoring, prescriptive programming and implementation of virtual electrophysiological functions remotely. Additionally, as discussed hereinabove, data center 62 includes other resources and features to provide remote monitoring, maintenance and upgrade of programmer 20. The location of remote data center 62 is dependent upon the sphere of service. In accordance with the present invention, data center 62 may be located in a corporate headquarters or manufacturing plant of the company that manufactures programmer 20. Further, the wireless data and electronic communications link/connection can be one of a variety of links or interfaces, such as a local area network (LAN), an internet connection, a telephone line connection, a satellite connection, a global positioning system (GPS) connection, a cellular connection, a laser wave generator system, any combination thereof, or equivalent data communications links.

As stated hereinabove, bi-directional wireless communications 109 acts as a direct conduit for information exchange between remote data center 62 and programmer 20. Further, bi-directional wireless communications 109 provides an indirect link between remote data center and IMDs 10, 10' and 10" via programmer 20. In the context of this disclosure the word "data" when used in conjunction with bi-directional wireless communications also refers to sound, video and information transfer between the various functional units.

Figure 6:
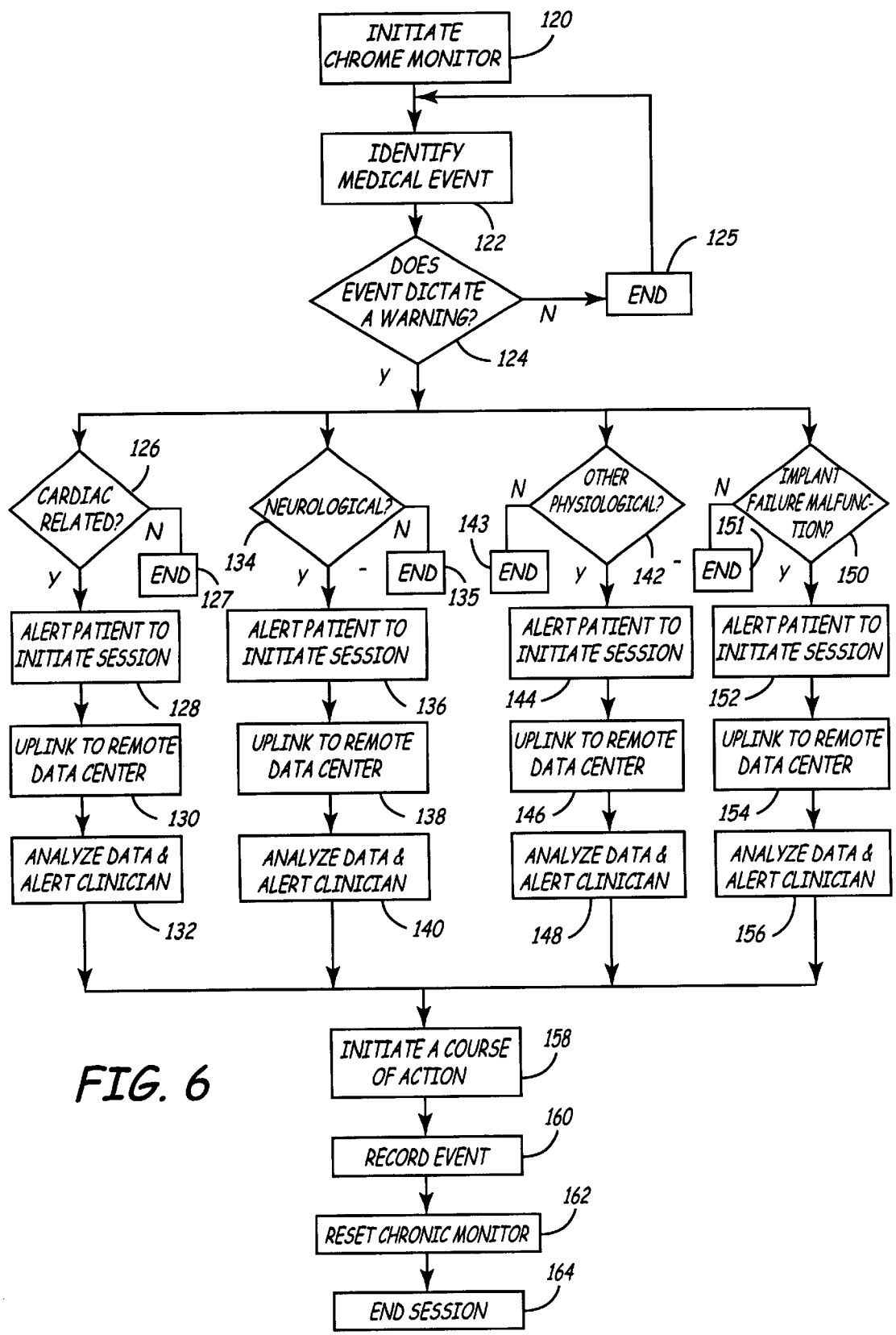
FIG. 6 represents a high level software logic for implementing chronic monitoring functions in the system of the present invention.

Referring to FIG. 6, a logic flow chart implementing the software for running CMM 102 is displayed. Specifically, the software logic is implemented by initiating CMM 102 under logic step 120. The logic identifies a medical event under logic step 122. This is primarily done by communicating to IMDs 10, 10' and 10" via programmer 20 and or IMU 20' to determine a prevailing medical condition. In a consequent logic step, the program goes into decision step 124 where the need for a warning, based on the medical event noted, is evaluated. If the evaluation indicates that the event does not require the issuance of a warning, the logic step will end the query under logic step 125 and may go into a waiting subroutine for the next signal. In the alternate, if a warning is warranted, the program proceeds to evaluate the need for whether the event relates to cardiac, neurological, other physiological and/or failure of any of the IMDs. Under the warning process, the program will advance to decision step 126 to check if the alert relates to cardiac data module 114. If not the query is terminated at step 127. If the alert relates to cardiac data module 114, however, the program logic proceeds to logic step 128 where the patient is alerted to initiate a session. The alert is sent via the two way communication links from web-enabled data center 62 to either programmer 20 or IMU 20'. Accordingly, one or all of IMDs 10, 10' and 10" are up-linked to remote data center 62 under logic step 130. Particularly, the data is directed to cardiac data module via selector 11 in analyzer 106. Thereafter, the data is analyzed and the clinician notified under logic step 132. Similarly, if the warning or medical event relates to neurological clinical care or therapy, the logic proceeds to decision step 134. The query is terminated if the medical event is not neurological. If neurological, however, the logic proceeds to logic step 136 to prompt the patient to initiate a session. Under this scenario, the patient uplinks to data center 62 via programmer 20 or IMU 20" which process is described under logic step 138. Specifically, the data is routed via selector 116 to neurological data module 112 where the data is analyzed and the physician or clinician is alerted in accordance with logic step 140. Similarly, if the medical event relates to other physiological diagnosis and clinical care, the logic proceeds to decision step 142. Consistent with the program logic described hereinabove, the logic proceeds to end the query under step 143 if the medical event does not relate to physiological aspects of the clinical care regimen. If it concerns physiological aspects, however, the program logic proceeds to logic step 144 to alert the patient to initiate a session. The patient's device is then up-linked to remote data center 62 under logic step 146. Subsequently, the data is analyzed and a clinician is alerted under logic step 148. Similarly, if the medical event relates to a noted malfunction or failure of any one or all of IMDs 10, 10' and 10", the program logic proceeds to decision block 150. The patient is alerted under logic step 152. Subsequently, the data is transferred from the IMD or IMDs in question to data center 62, under logic step 154, in the manner described hereinabove. The data is then analyzed and a clinician notified under logic step 156.

Thereafter, depending on the medical event at hand which may include one, all or any combinations thereof, the system will initiate a course of action under logic step 158. The event is recorded under step 160. Thereafter, the chronic monitor is reset under logic step 162 and the session ends at logic step 164.

The implementation of a chronic monitoring scheme is one of the significant features of the wireless communications and data exchange system advanced by the present invention. Specifically, chronic monitoring is implemented via CMM 102 that contains the software to manage the data stream from any of the IMDs on a real time basis. Further, the system enables the development of a data bank as it relates to both the therapy and diagnostic aspects of the IMDs. Selector 116 routes data input from CMM and further enables routing the data to the relevant module, i.e, device diagnosis module 108, physiological data module 110, neurological data module 112 and cardiac data module 114. CMM 102 is in data communications with programmer 20 and IMU 20'. Further, IMDs 10, 10' and 10" are preferably in data communications with programmer 20 and IMU20'. In the preferred embodiment, IMU 20' could be a handheldable web top device with telemetric communication capabilities to exchange data to and from IMDs 10, 10' and 10". Thus, IMU 20' could be a low-level version of programmer 20 having, for example, the ability to interact with IMDs 10, 10' and 10". Accordingly, CMM may monitor IMDs 10, 10' and 10" remotely through programmer 20 and/or IMU 20' via wireless links 109 and 107 respectively. In an alternate embodiment, IMU 20' may operate as an intermediate data exchange unit located with the patient. In this context, programmer 20 may be located remotely and would be in communication with IMU 20' and would be used to interact with data center 62.

Figure 7A:
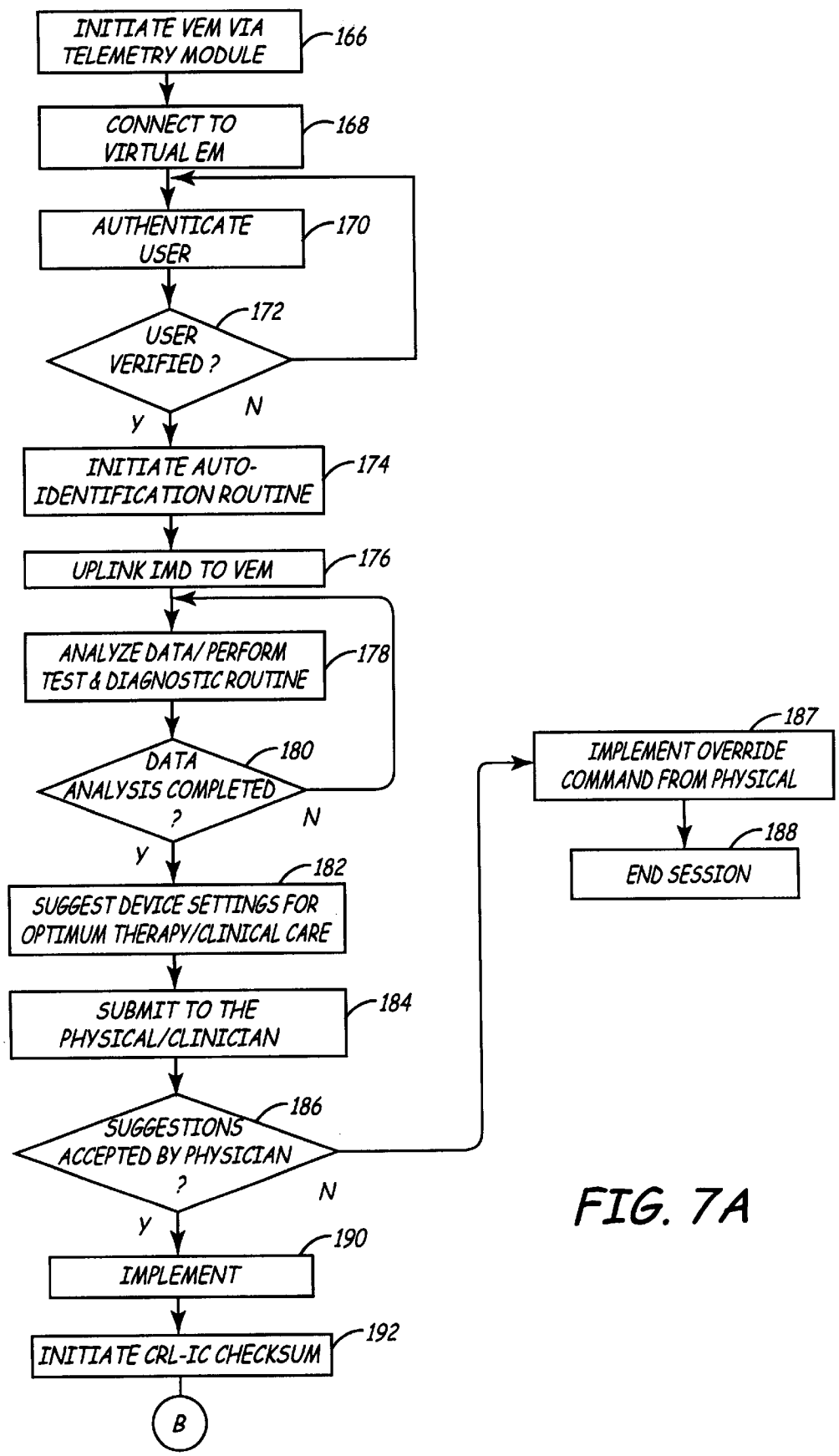
FIGS. 7A and 7B represent a high level software logic for implementing a virtual electrophysiologist module.
Figure 7B:
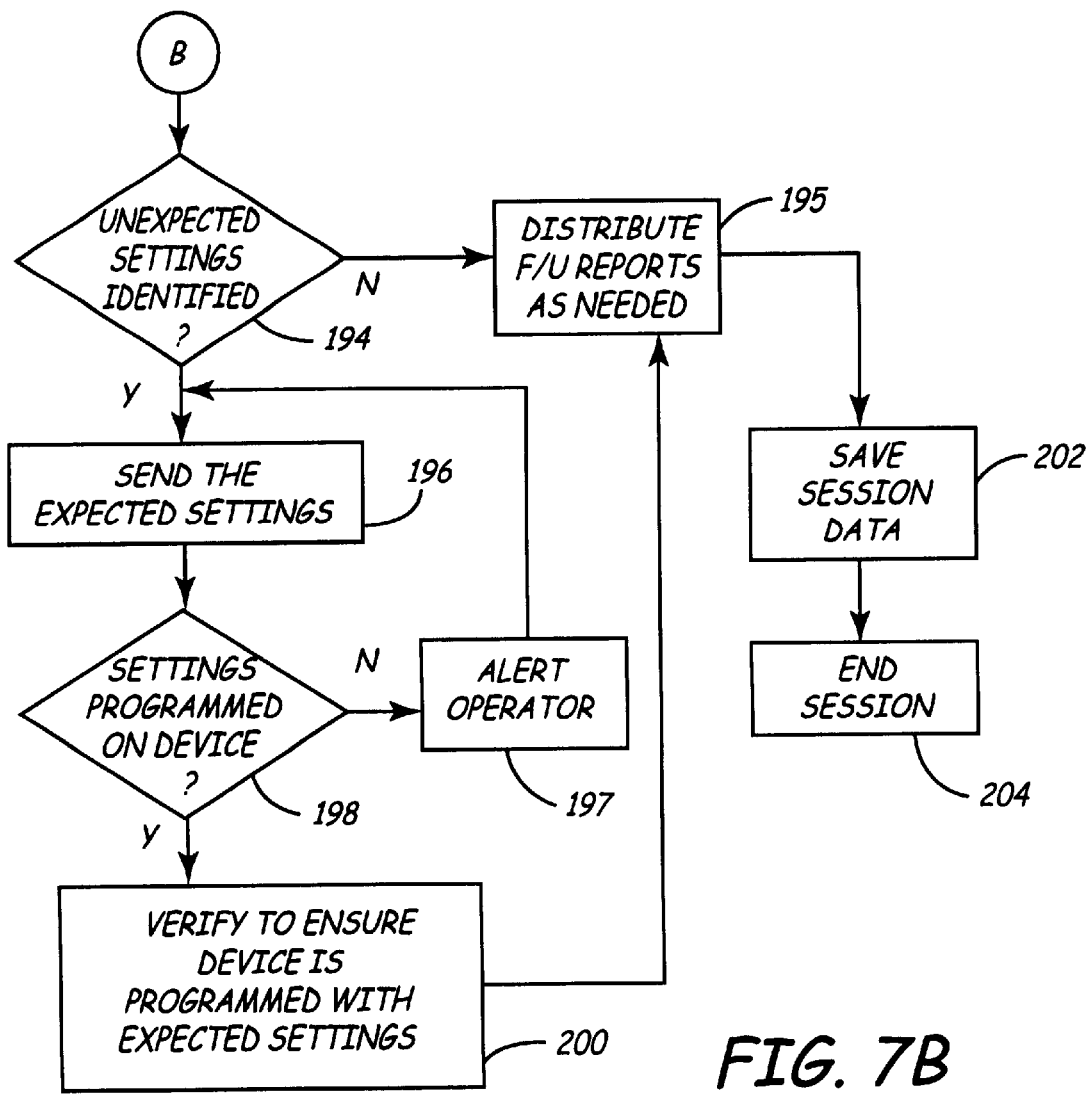

Referring to FIGS. 7A and 7B, a software logic chart is represented showing the implementation of VEM 100 to effect a continuous monitoring of IMDs 10, 10' and 10" for remotely adjusting the settings of the implanted devices to promote optimum therapy and clinical care. The logic starts at step 166 where VEM 100 is initiated via telemetry or equivalent wireless communication system. Subsequently, under logic step 168 either programmer 20 or IMU 20' is connected to VEM 100. Further, the user is authenticated, under logic step 170, before further access to information and operations in remote data center 62 is permitted. The logic proceeds to decision block 172 to check if the user has been verified. It should be noted that VEM 100 is used as a continuous, follow-up or real time system to enable adjustment of critical parameters of IMDs 10, 10' and 10" in real-time. Returning to decision block 172, if the user is not verified, the logic reverts back to step 170 where authentication of the user is requested. If after a few trials the user is not verified, the program terminates and displays a message asking the user to call the operator or some other authority. In the event the user is authenticated, the logic proceeds to step 174 where the auto identification routine is activated. Hereafter, the logic proceeds to uplink IMDs 10, 10' and 10" to VEM 100 via telemetry or equivalent wireless communications system. It should be noted that VEM 100 is connected to IMDs 10, 10' and 10" indirectly via programmer 20 and/or IMU 20". When IMDs 10, 10' and 10" are up-linked to VEM 100, access to the data base and information exchange is effected. Primarily, VEM 100 operates on data relating to the functional aspects of components in the IMDs. More specifically, VEM 100 monitors and is able to virtually and in real-time, review the status of designated components of the IMDs. Accordingly under logic step 178, the program logic sets to analyze data and perform tests and diagnostic routines. Subsequently, the program logic checks to see whether the data analysis is completed under decision block 180. If the analysis is incomplete, the logic reverts back to step 178. If the analysis is completed, a recommendation is made for device settings to deliver optimal therapy or clinical care under logic step 182. The recommendation is submitted to the physician or clinician under logic step 184. The physician renders an opinion, under decision block 180, as to whether the recommendation is acceptable based on current medical practice or accepted standards relating to the setting and the therapy or care for which the settings are to be made. If the recommendation is not accepted or approved by the physician, the software logic advances to logic step 187 where an override is set to implement the recommendation of the physician as to the desirable settings and the session is terminated at logic step 188. In the alternative, if the physician approves the recommendation it is implemented under logic step 190. Subsequently, the logic proceeds to step 192 where a CRC-checksum is used to make sure that the data has not changed or is false. Preferably, the CRC is a 16 bit and is created by initializing a checkvariable to set the CRC-checksum. The logic proceeds to decision block 194 where the software checks for any unexpected settings which may be identified. At this point in the logic, the system utilizes a redundant data check, via the CRC and decision block 194 to ensure that the remote setting data is accurate and uncorrupted. If an unexpected setting is identified, the logic proceeds to step 195 where a follow-up report (F/U) is distributed to the physician and other personnel for review and investigation of the unexpected settings and the source of the data corruption. Thereafter, the system saves the session data under logic step 202 and the session terminated at step 204. In the alternative, if no unexpected settings are identified, the expected settings are sent, under logic step 196, to the device via telemetry or equivalent wireless communications system. Subsequently, the logic advances to decision step 198 where the system checks if the remotely transferred settings data has been implemented on one or more of IMDs 10, 10' and 10", via programmer 20 or IMU 20', as needed. If not, the operator is alerted under logic step 197, and also may attempt to send the data again by reverting back to logic step 196. After a predetermined number of attempts to send the data, the system interrupts the sequence and will post a note to the operator. If programmer 20 and/or IMU 20' are programmed, the system checks to verify if IMDs 10, 10' and 10" are programmed with the respective expected settings under logic step 200. Thereafter, the logic proceeds to distribute follow up reports as needed under logic step 195. The session data and file history is saved under step 202. Subsequently, the session is terminated under logic step 204.

Accordingly VEM 100 is implemented to remotely monitor the settings of a plurality of medical devices in a patient. Particularly, VEM 100 is located remotely in a preferably web-enabled high capacity and high speed computer environment such as data center 62. VEM 100 operates as one of the therapeutic/clinical arms of the present invention. VEM 100 specializes in monitoring the critical and optimal settings in medical devices on a continuous basis. This is particularly important in patients with multi-implants because the range of settings of one device may not be compatible with the settings of other devices. Thus, VEM 100 is implemented to set, co-ordinate and monitor the various settings in a multi-implant medical device environment.

Figure 8A:
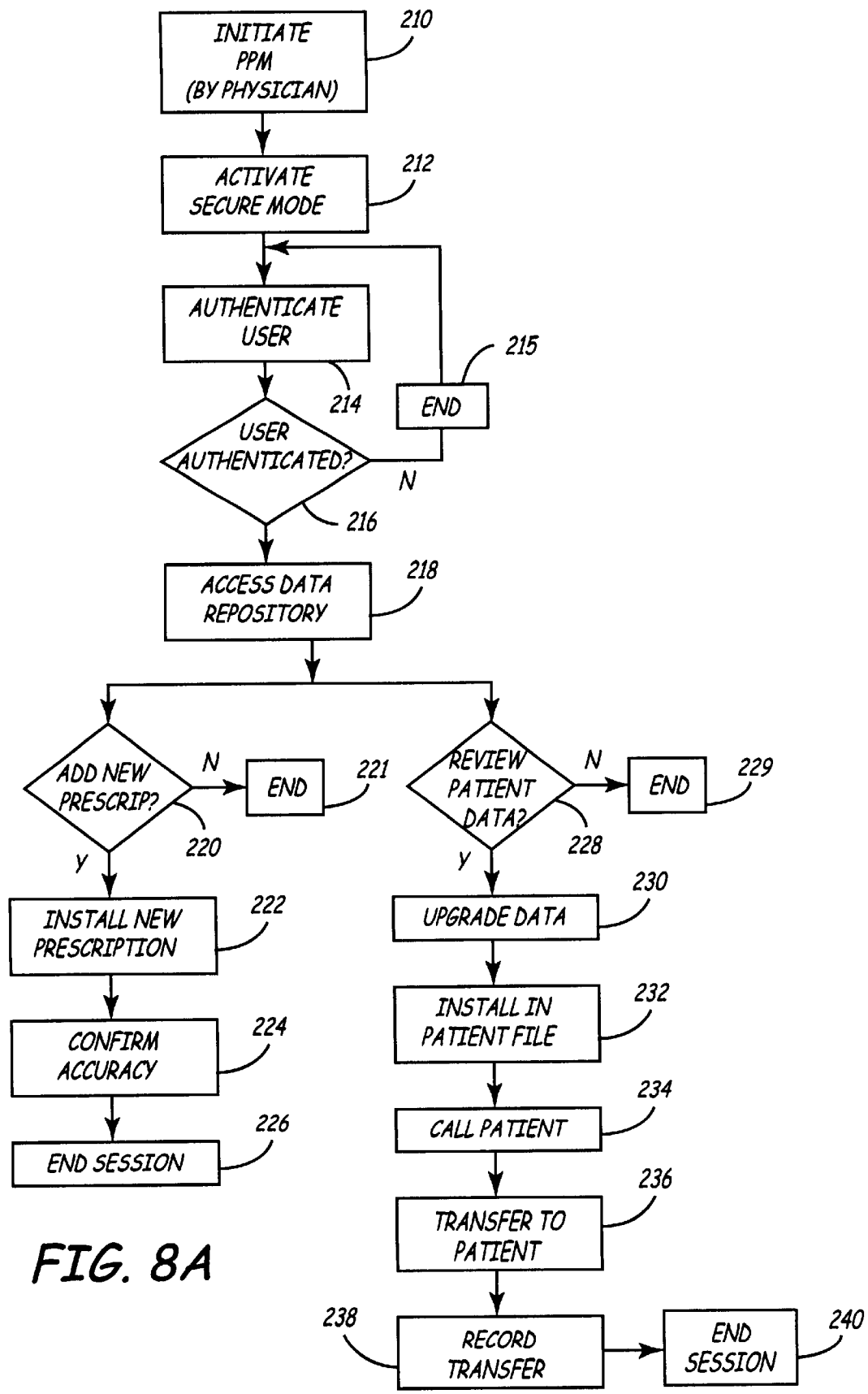
FIGS. 8A and 8B represent a high level software logic for implementing a prescriptive or therapy related program.
Figure 8B:
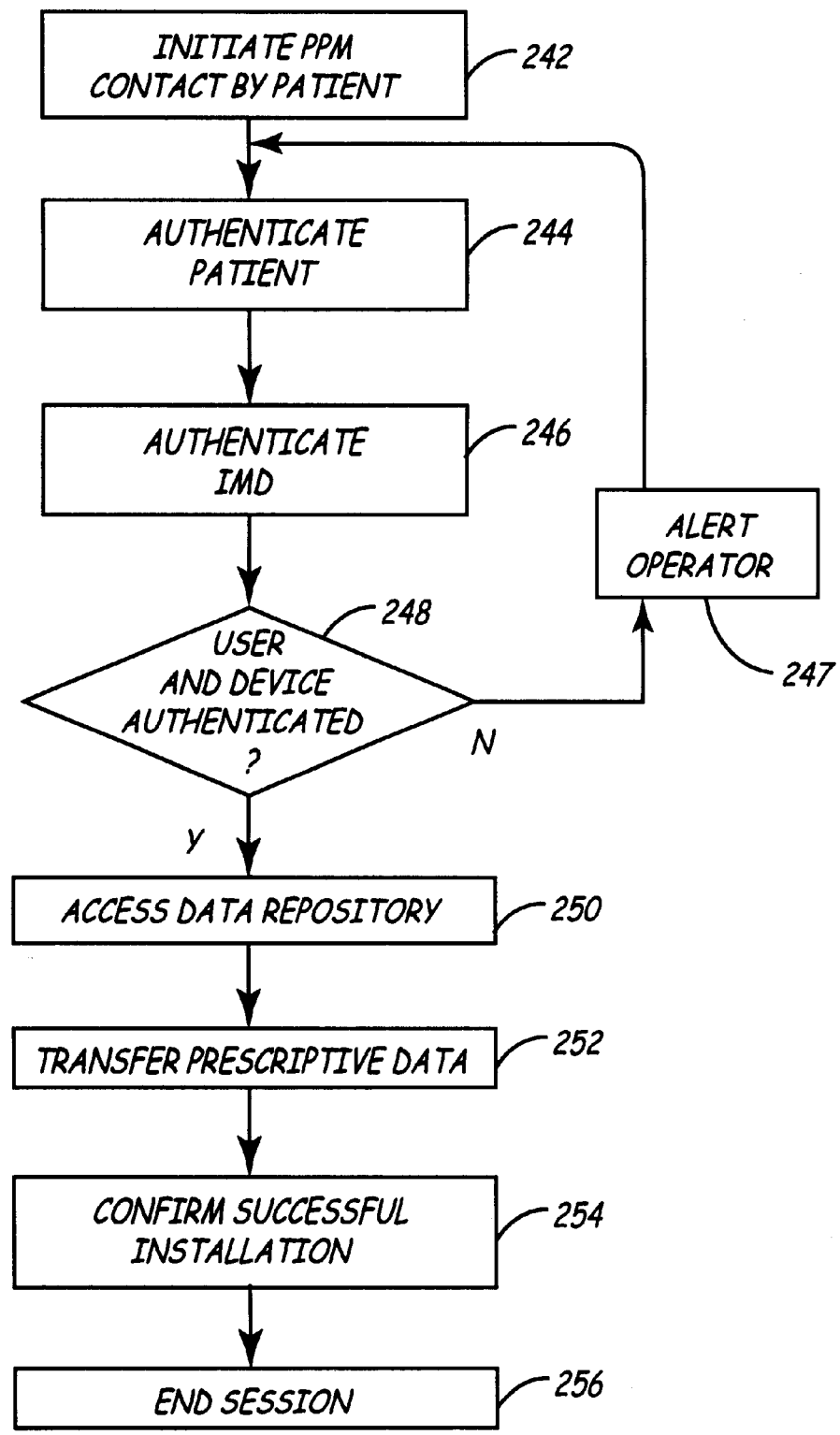

Referring to FIGS. 8A and 8B, the operation of PPM 104 is shown. As discussed hereinabove, PPM 104 relates to a remote programming of IMDs 10, 10' and 10" to install prescriptive functions. Specifically, the scheme relates, inter alia, to the remote installation of data that is in a repository as part of a recommended medical upgrade or alterations to IMDs 10, 10' and 10".

The PPM software is initiated by the physician under logic step 210. Subsequently under logic step 212 a secure mode is activated which includes encrypted operative to ensure security. The user is then authenticated under logic step 214. The secure mode triggers decision step 216 where the authenticity of the user is verified. If not verified the session is terminated under logic step 215. If the user is authenticated, access to an existing data repository is allowed under logic step 218. The menu includes an option to add new prescription data under decision block 220. If the session does not concern the addition of new prescription data, the logic proceeds to step 221 and the session is terminated. However, in the event a new prescription is to be added, the logic proceeds to install the required data under logic step 222. Thereafter, the accuracy of the data is confirmed under logic 224. The session for installing a new set of prescription data ends at logic step 226.

In the alternate, if the session concerns the review of patient data to ultimately install prescriptive data and/ or review the data to develop a new set of prescriptive data based on the performance history of IMDs 10, 10' and 10"; the menu provides the option to move to decision step 228. If that option is not selected, the session terminates at step 229. In the event the user elects to review the patient data and ultimately install a prescriptive program as needed, the logic proceeds to step 230 where the data is upgraded, altered or enhanced based on the patient history and other clinical parameters and decisions. The alterations and modifications are installed in the patient file under logic step 232. Thereafter, the physician will call the patient under logic step 232 to inform to the patient that a new program will be installed remotely. Consequently the new program is transferred via wireless communication systems, in the manner described hereinabove, under logic step 236. The transfer is then recorded under logic step 238 and the session terminates at logic step 240.

In an alternate embodiment, after the physician notifies the patient of the need to install an new program, the patient may initiate contact with PPM 104 to transfer the recommended data. Accordingly, referring to FIG. 8B, the patient initiates contact under logic step 242. The system authenticates the patient under logic step 244. Further the system authenticates the IMD or IMDs which are implanted in the patient. The logic proceeds to decision step 248 to determine if both the patient and the IMD or IMDs are authenticated to access the specific patient data and the relevant prescriptive program file. If such is not the case, the system alerts the operator under logic step 247 and denies access to the user. If, however, both the user and the IMD or IMDs are authenticated, access to data repository is allowed under logic step 250. Prescriptive data is then remotely transferred under logic step 252. Further, successful installation is confirmed under step 254. Logic step 254 contains subsets wherein if a successful installation is not confirmed after a predetermined number of attempts, a flag will be set to alert the operator and terminate the session after informing the patient about system malfunctions. Once a successful installation is confirmed, however, the logic proceeds to step 256 where the session terminates.

Thus, PPM 104 provides a set of data that is prescriptive in nature. Specifically, the PPM data set relates to clinically recommended upgrades and modifications which are integrated with patient history, performance of IMD/IMDs in the patient and similar clinical data. Generally, in the context of the present invention, prescriptive data is updated and upgraded by the physician thus forming a medical data repository specific to the patient and the devices implanted in the patient. When the need to install a new prescriptive program arises, the remote installation session may be initiated by the physician or the patient. When initiated by the physician, the patient needs to be informed such that either programmer 20 or IMU 20' could be set to accept the prescriptive data via wireless communication system, in the manner described hereinabove. The prescriptive program will then be transferred from programmer 20 and /or IMU 20' via telemetry communications with IMDs 10, 10' and 10".

Accordingly, the present invention provides a plurality of co-operative and complementary software programs implemented in a web-enabled high speed computer system to remotely monitor, manage and modify the operational and functional parameters of a plurality of implanted medical devices in a patient on a real-time basis. A high speed wireless data communications scheme is used to promote data exchange and transfer between remote data center 62 and IMDs 10, 10' and 10". IMDs 10, 10' and 10' are accessed via programmer 20 or IMU 20' which are locally placed to be within a telemetric communications range. VEM 100, CMM 102 and PPM 104 enable remote and continuous monitoring to identify a critical medical event, determine medical device setting and install prescriptive programs in a plurality of medical devices. The various software programs are integrated to provide a seamless real-time management of implanted medical devices to promote efficient and real-time clinical care and therapy remotely.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. An interactive remote diagnostics, monitoring and prescriptive programming system wherein a remote web-based expert data center is linked to a web-compatible interface medical device for an implantable medical device (IMD) to implement programming of the IMD, the system comprising:

a web-compatible interface medical device providing data communication with the IMD over a telemetry link;

a remote web-based expert data center; and a bi-directional communication link established on demand between the web-compatible interface medical device and the remote web-based expert data center;

the web-compatible interface medical device accessing the remote web-based expert data center in real time via the bi-directional communication link and accessing the IMD in real time via the telemetry link;

the remote web-based expert data center having a plurality of software modules operating to collect, manage, perform high-yield chronic evaluation and analysis for providing real time delivery of clinical care and therapy to a patient, wherein one of the software modules includes a virtual electrophysiologist module (VEM) to provide monitoring of IMD data relating to operational and functional parameters of the IMD and to provide data to adjust operational and functional parameters of the IMD;

the VEM having program logic to analyze the IMD data, perform tests on the data, and execute diagnostic routines based on the data;

the VEM being adapted to provide a recommendation for adjustments to the IMD operational and functional parameters; and the VEM including a physician activated override to modify the recommendation for adjustments to the operational and functional parameters of the IMD.

2. The system of claim 1 wherein the VEM module includes program logic to store a data analysis session.

3. The system of claim 1, wherein the interface medical device acquires patient data from the IMD.

4. The system of claim 1, wherein the bi-directional communication link is a telephone line.

5. The system of claim 1, wherein the bi-directional communication link is an intranet connection.

6. The system of claim 1, wherein the bi-directional communication link is an internet connection.

7. The system of claim 1, wherein the bi-directional communication link is a satellite connection.

8. The system of claim 1, wherein the bi-directional communication link is a global positioning system connection.

9. The system of claim 1 wherein the interface medical device is a programmer for the IMD.

10. The system of claim 1 wherein the interface medical device is a programmer for an implantable cardiac rhythm management device.

11. An interactive system wherein a remote web-based expert data center is linked to at least one web-compatible interface medical device for at least one implantable medical device (IMD) to implement remote chronic monitoring of a patient, the system comprising:

at least one web-compatible interface medical device providing data communication with at least one IMD over a telemetry link;

a remote web-based expert data center; and a bi-directional communication link established on demand between the at least one web-compatible interface medical device and the remote web-based expert data center;

the at least one web compatible interface medical device accessing the remote web-based expert data center in real time via the bi-directional communication link and accessing the at least one IMD in real time via the telemetry link;

the remote web-based expert data center having a plurality of software modules wherein one of the software modules includes a chronic monitoring module (CMM) to provide chronic monitoring of a patient by obtaining data relating to a medical event from the at least one IMD via the at least one web compatible interface medical device;

the CMM being adapted to evaluate the medical event and determine if a warning alert is needed and if the medical event is related to a cardiac event; and the CMM being adapted to provide a warning alert to the at least one web compatible interface medical device over the communication link.

12. The system of claim 11 wherein the CMM provides a clinician alert and routes the data relating to a medical event for analysis by a clinician.

13. The system of claim 11 wherein the CMM evaluates the data to determine whether the medical event concerns physiological aspects of a clinical care regimen for a patient.

14. The system of claim 11 wherein the CMM evaluates the data to determine whether the medical event concerns a malfunction of the IMD.

15. The system of claim 11 wherein the web-compatible interface medical device provides data communication with an implantable cardiac rhythm management device.

16. An interactive system wherein a remote web-based expert data center is linked to a web-compatible interface medical device for an implantable medical device (IMD) to implement programming of prescriptive functions in the IMD, the system comprising:

a web-compatible interface medical device to provide data communication with an implantable medical device over a telemetry link;

a remote web-based expert data center; and a bi-directional communication link established on demand between the web-compatible interface medical device and the remote web-based expert data center;

the interface medical device accessing the expert data center in real time via the bi-directional communication link and accessing the implantable medical device in real time via the telemetry link;

the remote web-based expert data center having a physician activated prescriptive programming software module to install a new prescriptive function in the IMD over the communication link via the interface medical device.

17. The system of claim 16 wherein the web-compatible interface medical device provides data communication with an implantable cardiac rhythm management device.

18. An interactive system wherein a remote web-based expert data center is linked to a web-compatible interface medical device for an implantable medical device (IMD) to implement programming of the IMD, remote chronic monitoring of a patient, and programming of prescriptive functions in the IMD, the system comprising:

a web-compatible interface medical device to provide data communication with an implantable medical device over a telemetry link;

a remote web-based expert data center; and a bi-directional communication link established on demand between the web-compatible interface medical device and the remote web-based expert data center;

the interface medical device accessing the expert data center in real time via the bi-directional communication link and accessing the implantable medical device in real time via the telemetry link;

the remote web-based expert data center having a software module providing real time clinical care and therapy to a patient by obtaining data relating to operational and functional parameters of the implantable medical device for diagnosis and providing data to adjust the operational and functional parameters of the implantable medical device to promote optimal delivered therapy to the patient;

the remote web-based expert data center having a software module providing chronic monitoring of a patient by obtaining data relating to a medical event from the implantable medical device via the interface medical device for evaluation and providing a warning alert to the interface medical device over the communication link;

the remote web-based expert data center having a physician activated prescriptive programming software module to install a new prescriptive function in the IMD over the communication link via the interface medical device.

19. The system of claim 18 wherein the web-compatible interface medical device provides data communication with an implantable cardiac rhythm management device.

* * * * *